United States Patent [19]

Goodman

[11] Patent Number: 4,849,558

[45] Date of Patent: Jul. 18, 1989

[54] PURIFICATION OF CHLOROFLUOROCARBONS

[75] Inventor: Walter H. Goodman, Villa Park, Ill.

[73] Assignee: Allied-Signal Inc., Morristown, N.J.

[21] Appl. No.: 213,745

[22] Filed: Jun. 30, 1988

[51] Int. Cl.$^4$ .................. C07C 17/38; C07C 19/08
[52] U.S. Cl. .................................................. 570/179
[58] Field of Search .......................................... 570/179

[56] References Cited

U.S. PATENT DOCUMENTS

| | | | |
|---|---|---|---|
| 2,149,039 | 2/1939 | Benning et al. | 570/179 |
| 2,879,228 | 3/1959 | Holeton | 208/310 |
| 2,909,570 | 10/1959 | Wade et al. | 570/179 |
| 3,696,156 | 10/1972 | Weeks | 260/648 F |

FOREIGN PATENT DOCUMENTS

| | | |
|---|---|---|
| 3017531 | 11/1981 | Fed. Rep. of Germany . |
| 3311751 | 10/1984 | Fed. Rep. of Germany ...... 570/179 |
| 48-103502 | 12/1973 | Japan . |
| 58-035737 | 8/1983 | Japan . |
| 743985 | 6/1983 | U.S.S.R. . |

*Primary Examiner*—J. E. Evans
*Attorney, Agent, or Firm*—Harold N. Wells; Jay P. Friedenson

[57] ABSTRACT

Chlorofluorocarbon solvents, particularly R113, may be purified by removing $SO_2$ or its equivalent to the level of below about 0.3 ppb by contact with alumina or zeolites.

13 Claims, No Drawings

4,849,558

PURIFICATION OF CHLOROFLUOROCARBONS

This invention relates to purification of chlorofluorocarbons. More particularly, it relates to removal of trace impurities from chlorofluorocarbons used for cleaning electronic devices during their manufacture.

PRIOR ART

Purification of halogenated hydrocarbons has been the subject of many patents. Generally, these relate to removing reaction by-products which are difficult to remove by ordinary methods, especially partially halogenated hydrocarbons which still contain one or more hydrogen atoms.

In U.S. Pat. No. 2,879,228 such hydrogen-containing impurities are removed by contact with alumina or silica gel at a temperature of 100° to 250° C. The impurities are adsorbed by the alumina or silica, leaving a purified perfluorinated hydrocarbon.

Removing hydrogen-containing halogenated hydrocarbons also is the object of the process disclosed in Japanese patent application No. 48-103502. Sodium carbonate solutions are used to treat perchlorofluoroalkanes such as trichlorotrifluoroethane at 25°–60° C.

The use of alumina with 0.1 to 5% of an alkali metal or alkaline earth metal, as the hydroxide or oxide, to remove unsaturated impurities to below 2 ppm is the subject of U.S. Pat. No. 3,696,156.

Purification of contaminated refrigerants such as R113 (trichlorotrifluoroethane) by contact with alumina and an alkaline earth is discussed in West German DE3017531.

Zeolites have also been suggested as useful for purification of halogenated hydrocarbons. In West German DE No. 3311751 a zeolite having a pore size of 0.4–1 nm, such as the Ca form of zeolite A, is used to remove halogens and inorganic halides from fluorochlorocarbons, such as trichlorotrifluoroethane.

Japanese patent No. 83035737 relates to regeneration of a zeolite used to purify and dry trichloroethane.

Chlorinated and fluorinated organic solvents used to clean electronic components are purified by passing the solvents in the vapor phase over activated carbon in the presence of phosphorus pentoxide according to Russian patent SU No. 743985.

Very high purity solvents are used in cleaning electronic components. R113 (trichlorotrifluoroethane) is a solvent of choice in many such applications. It has been found that essentially undetectable amounts of impurities can result in corrosion of the parts to be cleaned. Consequently, identification of the offending impurities and their removal has presented a significant problem. The present invention relates to a solution of that problem.

SUMMARY OF THE INVENTION

Trace contamination of chlorofluorocarbon solvents such as R113 containing less than about 10 ppb, typically about 3 ppb (as sulfur), of sulfur compounds may be reduced below the 0.3 ppb level by contacting the solvent with an adsorbent for sulfur compounds at ambient temperature, say about 20° to 45° C., for a period of time sufficient to reduce the sulfur compounds in the solvent to the desired level. The amount of sulfur compounds refers to those remaining in a sample of solvent which has been reduced to about 1/200 of its original volume and therefore does not include any sulfur compounds which are removed during concentration of the sample.

Preferred adsorbents are alumina and zeolites. Improved capacity for sulfur compounds is obtained by pretreating the alumina with air at about 600° C. or prewashing with an aqueous sodium hydroxide solution and then air drying at about 400° C. Of the zeolites, the 13X type is preferred. The amount of adsorbent required will depend upon the level of sulfur desired. For 13X zeolite only about 0.008 gm per gm of solvent are sufficient whereas about 10 times more is required if untreated alumina is used.

DETAILED DESCRIPTION OF THE INVENTION

The Problem

Chlorofluorocarbons, particularly R113 (trichlorotrifluoroethane), are widely used for cleaning electronic parts. Clearly, while the solvent used must remove contaminants such as grease, it must not leave deposits of impurities found in the solvent. In addition, it should clean the subject part and not cause any changes to the surface to which the solvent is applied. Thus, extremely pure solvents are used, typically having no more than about 10 ppm of impurities such as water and trace amounts of contaminants derived from the production of the solvent, such as sulfur compounds. In general, the previous patents discussed above relate to purification of halogenated hydrocarbons to a level which is useful for most applications, but not for those requiring extremely pure solvents. It has now been found that very small amounts of sulfur compounds, that is, below about 10 ppb, typically about 3 ppb, which is well below the usual level of detectability can still cause problems in use.

It was found that corrosion was occurring during the cleaning of electronic parts even though there was apparently no detectable contaminant present which could cause such corrosion. By reducing a sample of the solvent by a factor of 3333/1 and analyzing the resulting sample by mass spectroscopy, it was found that sulfur dioxide (or a related compound which releases sulfur dioxide) was present at a level of about 3 ppb. However, it is to be understood that reference to sulfur dioxide is meant to refer to the sulfur compounds detected without regard to the actual chemical formula. Once the amount and identity of the source of corrosion was discovered, it remained to determine how it could be removed when at such a low level.

A test for sulfur compounds has been used which will be described later. A sample of solvent is concentrated to 1/200 of its original volume, thus raising the level of sulfur and permitting analysis. Since a substantial amount of solvent must be removed, it is possible that the fresh solvent contains larger amounts of sulfur in a volatile form, for example, additional $SO_2$, which vaporized during the concentration. Thus, wherever it is stated herein that a sample contained a small amount of a sulfur compound, e.g. 1 ppb, it should be understood that the analysis was made on a concentrated sample and does not necessarily mean that the original sample actually contained only that small amount, although that is believed to be true.

Sulfur Removal

Although adsorbents have been suggested for removing various contaminants resulting from manufacture and use of halogenated solvents, it is not clear that they could satisfactorily remove sulfur compounds at the 3 ppb (as sulfur) level down to about 0.3 ppb or below. It has now been found that within certain parameters some solid adsorbents can be successfully employed to purify such solvents and in particular R-113 which must satisfy stringent purity requirements. Although the solvent typically will initially contain about 10 ppb of sulfur compounds or below, the maximum permissible is not known. It should be determined by the capacity of the adsorbents, that is, a large amount of sulfur in the fresh solvent would prevent the adsorbent from achieving the very low concentration of sulfur required for critical cleaning applications.

The properties required of adsorbents which are used to remove sulfur compounds to such low levels can be identified as follows. First, they must have a satisfactory capacity for sulfur compounds even when in contact with a solvent having about 0.1 ppb or less. Second, they must not contribute any other contaminant to the solvent while removing sulfur. Third, they must be reasonably economic to use. Finally, the quality of the adsorbent should be consistent since it may be difficult to measure its capacity for sulfur compounds.

One problem which is inherent in removing impurities at such low levels is how one is to accurately measure the impurity. As previously indicated, it is generally necessary to reduce the volume of a sample in order to raise the concentration of the impurity so that it can be measured. This must be done in such a manner that the impurity is not inadvertently removed in part, making the results inaccurate. At the same time, the method of reducing the volume should not create impurities. In practice, it has been found that reducing a sample of the solvent by evaporation provides satisfactory results. As previously discussed, it is believed that even if some sulfur compounds are removed during evaporation that the residual solvent contains the sulfur compounds responsible for corrosion when the solvent is used to clean electronic parts. Consequently, reduction of a sample of the solvent not only makes analysis of the sulfur content possible, but at the same time removes the sulfur compounds which should not be measured.

Analysis is difficult at the lower edge of detectability. Several methods may be used. One method which is useful involves the treatment of a sample of reduced solvent with a $KI-I_2-NaN_3$ solution to produce nitrogen gas. The number of bubbles of gas which form are related to the amount of sulfur present. It has been found that 50 bubbles corresponds to about 0.637 ppb of sulfur in a 1000 ml original sample which has been reduced by 1/200 to 5 ml, from which a 1 ml sample is analyzed. The 1 ml sample is deposited on a silvered glass microscope slide and evaporated. Then the residue is contacted with an aqueous solution of 5.2 wt. % $KI/I_2/NaN_3$, having a molar ratio of 1.4/1/9.2. The reaction takes place at about ambient temperature, say in the range of 20°–45° C. The bubbles which form are counted and converted to the equivalent amount of sulfur.

EXAMPLE 1

A 1000 ml sample of R113 is evaporated by boiling from a two-liter flask until 5 ml remains. A one ml portion of reduced sample is analyzed using the method described above. The sulfur content is found to be >3 ppb based on the volume of the original sample. Analysis by mass spectroscopy indicates that $SO_2$ is the only sulfur species present and also that no other compounds are present which would be expected to cause corrosion.

EXAMPLE 2

The R113 analyzed in Example 1 is brought into contact with about 0.0078 gram of various adsorbents for each gram of solvent. The adsorbent is placed in a glass vessel, the solvent added, and the vessel shaken for 16 hours. The solvent is analyzed after contact with the adsorbent and the sulfur content determined following the procedures of Example 1. The results are shown in the following table.

| Adsorbent | Pretreatment | Sulfur Content |
|---|---|---|
| alumina(1) | none | >3 ppb |
| alumina(1) | dried in air at 600° C. | 0.9 ppb |
| alumina(1) | washed in 5N NaOH solution and dried in air at 400° C. | 0.5 ppb |
| zeolite 5A(2) | dried in air at 400° C. | >3 ppb |
| zeolite 5A(3) | dried in air at 400° C. | 2 ppb |
| zeolite 13X(4) | dried in air at 600° C. | 0.3 ppb |
| zeolite KX(5) | dried in air at 400° C. | >3 ppb |

(1)Grade A alumina supplied by Rhone-Poulenc
(2)5A molecular sieves supplied by Linde Div. of Union Carbide
(3)ADS-14 supplied by UOP Inc.
(4)ADS-2 supplied by UOP Inc.
(5)ADS-22 supplied by UOP Inc.

The results indicate that drying alumina increases its ability to remove sulfur compounds. Thus it would be expected that water from the solvent would accumulate on the alumina and interfere with its ability to adsorb sulfur compounds.

The 13X molecular sieve appears to have a greater capacity for sulfur compounds than the other zeolites tested and alumina.

The above results indicate the relative performance of the adsorbents tested but poorer capacity as with untreated alumina can be overcome if a greater quantity is used, as the following example shows.

EXAMPLE 3

A succession of six-gram samples of the untreated alumina of Example 2 are contacted with a 500 ml sample of R113 to determine the capacity necessary to successfully reduce the $SO_2$ content. It is found that about 0.07 gm of alumina per gram of R113 are sufficient to reduce the $SO_2$ content below 0.1 ppb, as indicated by the test discussed above.

What is claimed is:

1. A process for purifying chlorofluorocarbon solvents having an initial sulfur content of less than about 10 ppb comprising contacting said solvent with sufficient amount of an adsorbent for sulfur compounds for each unit weight of solvent at about ambient temperature for a period of time sufficient to remove said sulfur compounds in said solvent to a level of 0.3 ppb or below.

2. The process of claim 1 wherein the sulfur content is derived from sulfur dioxide or a compound which releases sulfur dioxide.

3. The process of claim 1 wherein the adsorbent is alumina.

4. The process of claim 3 wherein the amount of alumina is at least about 0.07 grams per gram of solvent.

5. The process of claim 3 wherein said alumina has been pretreated by air drying at about 600° C.

6. The process of claim 3 wherein said alumina has been pretreated by washing in aqueous sodium hydroxide solution and thereafter air drying at about 400° C.

7. The process of claim 1 wherein said adsorbent is a zeolite.

8. The process of claim 7 wherein said zeolite is a 5A molecular sieve.

9. The process of claim 7 wherein said zeolite is a 13X molecular sieve.

10. The process of claim 9 wherein the amount of 13X zeolite is at least about 0.008 gram per gram of solvent.

11. The process of claim 7 wherein said zeolite is a KX molecular sieve.

12. The process of claim 1 wherein said solvent is trichlorotrifluoroethane.

13. The process of claim 1 wherein the temperature is about 20°–45°0 C.

* * * * *

UNITED STATES PATENT AND TRADEMARK OFFICE
CERTIFICATE OF CORRECTION

PATENT NO.   : 4,849,558
DATED        : July 18, 1989
INVENTOR(S)  : Walter H. Goodman It is certified that error appears in the above-identified patent and that said Letters Patent is hereby corrected as shown below:

Column 2, line 11: "10times" to read --10 times--.
Column 6, line 10: "45°0C." to read --45°C.

Signed and Sealed this

Third Day of April, 1990

Attest:

HARRY F. MANBECK, JR.

*Attesting Officer*  *Commissioner of Patents and Trademarks*